US012691295B2

(12) United States Patent (10) Patent No.: US 12,691,295 B2

Wasserman (45) Date of Patent: Jul. 28, 2026

(54) SYSTEM AND METHOD FOR MAINTAINING TTFIELDS DURING BATTERY CHANGES

(71) Applicant: Novocure GmbH, Root (CH)

(72) Inventor: Yoram Wasserman, Haifa (IL)

(73) Assignee: Novocure GmbH, Baar (CH)

( * ) Notice: Subject to any disclaimer, the term of this patent is extended or adjusted under 35 U.S.C. 154(b) by 272 days.

(21) Appl. No.: 18/475,931

(22) Filed: Sep. 27, 2023

(65) Prior Publication Data

US 2024/0108908 A1 Apr. 4, 2024

Related U.S. Application Data

(60) Provisional application No. 63/377,642, filed on Sep. 29, 2022.

(51) Int. Cl.
*A61N 1/40* (2006.01)
*H01M 10/42* (2006.01)
*H02J 7/82* (2026.01)

(52) U.S. Cl.
CPC ............ *A61N 1/40* (2013.01); *H01M 10/425* (2013.01); *H01M 2220/30* (2013.01); *H02J 7/82* (2026.01)

(58) Field of Classification Search
CPC ...... A61N 1/40; A61N 1/36014; A61N 1/378; A61N 1/0476; A61N 1/36002; H01M 10/425; H01M 2220/30; H02J 7/0048
See application file for complete search history.

(56) References Cited

U.S. PATENT DOCUMENTS

| | | | |
|---|---|---|---|
| 2021/0162228 A1 | 6/2021 | Urman et al. | |
| 2021/0196967 A1* | 7/2021 | Carlson | A61N 1/36002 |
| 2022/0176102 A1* | 6/2022 | Pribula | A61N 1/36002 |
| 2024/0061398 A1* | 2/2024 | Hershkovich | B33Y 50/00 |

FOREIGN PATENT DOCUMENTS

CN 202844368 U 4/2013

OTHER PUBLICATIONS

International Search Report and The Written Opinion (PCT/IB23/059653), dated Feb. 5, 2024, 18 pages.

* cited by examiner

*Primary Examiner* — Catherine M Voorhees
(74) *Attorney, Agent, or Firm* — DUNLAP CODDING, P.C.

(57) ABSTRACT

An electronic apparatus is herein disclosed. The electronic apparatus comprises: an electric field generator providing a first electrical signal having a first alternating current waveform at a frequency between 50 kHz and 1 MHz; and a controller communicating with the electric field generator, the controller having an input, a processor, and a memory storing an accelerated power-up program, a standard power-up program, and computer-executable instructions that cause the processor to: receive a generator power-down event by the input; detect the generator power-down event; deactuate the electric field generator; store an operating parameter; determine an operating status based at least in part on the operating parameter; and actuate the electric field generator to provide a second electrical signal using the accelerated power-up program responsive to the operating status being the accelerated status; the second electrical signal having a second alternating current waveform at a frequency between 50 kHz and 1 MHz.

17 Claims, 4 Drawing Sheets

SYSTEM AND METHOD FOR MAINTAINING TTFIELDS DURING BATTERY CHANGES

CROSS REFERENCE TO RELATED APPLICATIONS

The present application claims priority to Provisional Patent Application U.S. Ser. No. 63/377,642 titled "SYSTEM AND METHOD FOR MAINTAINING TTFIELDS DURING BATTERY CHANGES" filed on Sep. 29, 2022, the entire contents of which are hereby expressly incorporated herein by reference.

BACKGROUND OF THE INVENTION

Tumor Treating Fields (TTFields or TTFs) are low intensity (e.g., 1-3 V/cm) alternating electric fields within the intermediate frequency range (e.g., 50 kHz to 1 MHz, such as 50-500 kHz) that target solid tumors by disrupting mitosis. This non-invasive treatment targets solid tumors and is described, for example, in U.S. Pat. Nos. 7,016,725; 7,089,054; 7,333,852; 7,565,205; 8,244,345; 8,715,203; 8,764,675; 10,188,851; and 10,441,776. TTFields are typically delivered through two pairs of transducer arrays that generate perpendicular fields within the treated tumor; the transducer arrays that make up each of these pairs are positioned on opposite sides of the body part that is being treated. More specifically, for the OPTUNE® system, one pair of electrodes of the transducer array is located to the left and right (LR) of the tumor, and the other pair of electrodes of the transducer array is located anterior and posterior (AP) to the tumor. TTFields are approved for the treatment of glioblastoma multiforme (GBM), and may be delivered, for example, via the OPTUNE® system (Novocure Limited, St. Helier, Jersey), which includes transducer arrays placed on the patient's shaved head. More recently, TTFields therapy has been approved as a combination therapy with chemotherapy for malignant pleural mesothelioma (MPM), and may find use in treating tumors in other parts of the body.

The OPTUNE® device is intended to be continuously worn by the patient for 2-4 days before removal for hygienic care and re-shaving (if necessary), followed by reapplication with a new set of arrays. Because patients use the device and go about their daily activities, the device may be used for an extended period of time when the patient is not near a power source. As such, the device may include a battery.

SUMMARY OF THE INVENTION

As discussed above, the OPTUNE® device may be used for an extended period of time when the patient is not near a power source. Traditionally, changing the battery requires shutting down the device and changing the battery. Because the system is shut down, the device has to go through the traditional initialization procedure, during which time, the TTField applied to the patient is initially supplied at a low power and slowly increased over a period of time of approximately 30 minutes to an operating power to ensure that the transducer arrays are properly applied to the patient and thereby avoid harming the patient (e.g., a standard power-up process). But supplying low power during the traditional initialization procedure reduces the amount of treatment that the patient receives.

Thus, new and improved systems that maintain the operating power and/or shorten the reinitialization time and provide a full-power TTField to the patient more quickly are desired (e.g., an accelerated power-up process), especially during battery changes. It is to such systems and methods of producing and using the same, that the present disclosure is directed.

The problem of shortening the reinitialization time and providing a full-power TTField to the patient is solved by an electronic apparatus for delivering TTFields to a body of a subject, the electronic apparatus comprising an electric field generator and a controller. The electric field generator is configured to provide a first electrical signal having a first alternating current waveform at a frequency in a range from 50 kHz to 1 MHz. The controller communicates with the electric field generator to control an output of the electric field generator. The controller has an input, a processor and a non-transitory computer-readable medium storing an accelerated power-up program, a standard power-up program, and computer-executable instructions that when executed by the processor cause the processor to: receive a generator power-down event by the input, the generator power-down event being a physical interaction with the input; detect the generator power-down event; deactuate the electric field generator so as to cease providing the first electrical signal; store an operating parameter indicative of an operation of the electric field generator or cessation of operation of the electric field generator; determine an operating status based at least in part on the operating parameter, the operating status being one of an accelerated status and a standard status; and actuate the electric field generator to provide: i) a second electrical signal using the accelerated power-up program responsive to the operating status being the accelerated status; the second electrical signal having a second alternating current waveform at a frequency in the range from 50 kHz to 1 MHz; or ii) a third electrical signal with the standard power-up program responsive to the operating status being the standard status, the third electrical signal having a third alternating current waveform at a frequency in the range from 50 kHz to 1 MHz.

The details of one or more implementations of the subject matter described in this specification are set forth in the accompanying drawings and the description below. Other aspects, features and advantages of the subject matter will become apparent from the description, the drawings, and the claims.

BRIEF DESCRIPTION OF THE DRAWINGS

The accompanying drawings, which are incorporated in and constitute a part of this specification, illustrate one or more implementations described herein and, together with the description, explain these implementations. The drawings are not intended to be drawn to scale, and certain features and certain views of the figures may be shown exaggerated, to scale or in schematic in the interest of clarity and conciseness. Not every component may be labeled in every drawing. Like reference numerals in the figures may represent and refer to the same or similar element or function. In the drawings.

DETAILED DESCRIPTION

Figure 1:
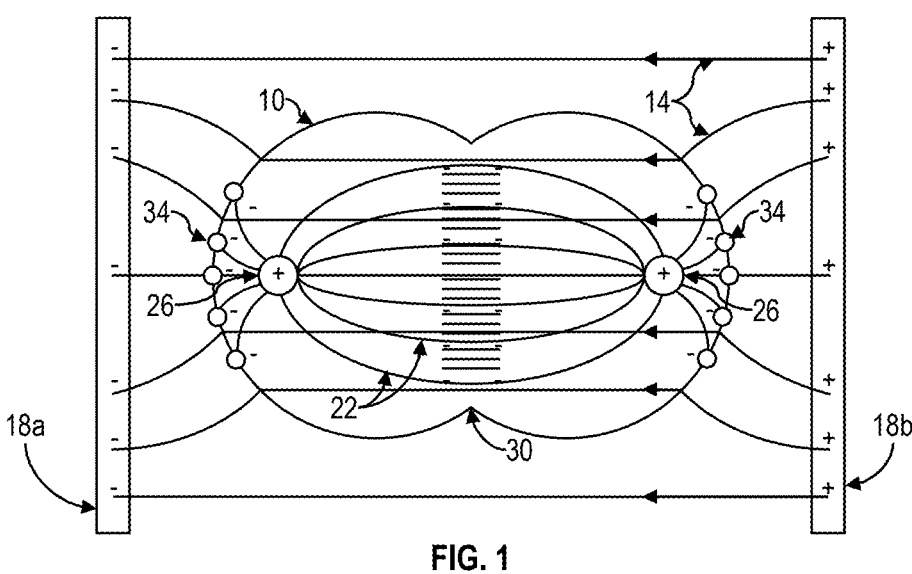
FIG. 1 is an exemplary embodiment of a schematic diagram of electrodes as applied to living tissue.

Before explaining at least one embodiment of the inventive concept(s) in detail by way of exemplary language and results, it is to be understood that the inventive concept(s) is not limited in its application to the details of construction and the arrangement of the components set forth in the following description. The inventive concept(s) is capable of other embodiments or of being practiced or carried out in various ways. As such, the language used herein is intended to be given the broadest possible scope and meaning; and the embodiments are meant to be exemplary—not exhaustive. Also, it is to be understood that the phraseology and terminology employed herein is for the purpose of description and should not be regarded as limiting.

Headings are provided for convenience only and are not to be construed to limit the invention in any manner. Embodiments illustrated under any heading or in any portion of the disclosure may be combined with embodiments illustrated under the same or any other heading or other portion of the disclosure. Any combination of the elements described herein in all possible variations thereof is encompassed by the invention unless otherwise indicated herein or otherwise clearly contradicted by context.

Unless otherwise required by context, singular terms shall include pluralities and plural terms shall include the singular.

All of the compositions, assemblies, systems, kits, and/or methods disclosed herein can be made and executed without undue experimentation in light of the present disclosure. Where a method claim does not specifically state in the claims or description that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification. Similarly, it is in no way intended that an order be inferred, in any respect, where computer-executed events resulting from computer-executable instructions are not specifically stated in the claims or description to be limited to a specific order.

The use of the term "a" or "an" when used in conjunction with the term "comprising" in the claims and/or the specification may mean "one," but it is also consistent with the meaning of "one or more," "at least one," and "one or more than one." The term "plurality" refers to "two or more."

In addition, the use of the term "at least one of X, Y, and Z" will be understood to include X alone, Y alone, and Z alone, as well as any combination of X, Y, and Z. The use of ordinal number terminology (e.g., "first," "second," "third," "fourth," etc.) is solely for the purpose of differentiating between two or more items and is not meant to imply any sequence or order or importance to one item over another or any order of addition, for example.

The use of the term "or" in the claims is used to mean an inclusive "and/or" unless explicitly indicated to refer to alternatives only or unless the alternatives are mutually exclusive.

As used herein, all numerical values or ranges include the end points, and fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., as well as sub-ranges, e.g., 2-8, within the greater range 1-10 and so forth.

Circuitry, as used herein, may be analog and/or digital components, or one or more suitably programmed processors (e.g., microprocessors) and associated hardware and software, or hardwired logic. Also, "components" may perform one or more functions. The term "component," may include hardware, such as a processor (e.g., microprocessor), an application specific integrated circuit (ASIC), a field programmable gate array (FPGA), a combination of hardware and software, and/or the like. The term "processor" as used herein means a single processor or multiple processors working independently or together to collectively perform a task.

A program, or software, may include one or more computer-executable instruction that when executed by one or more components, e.g., the processor, cause the component to perform a specified function. It should be understood that the processes and/or algorithms described herein may be stored on one or more non-transitory computer-readable medium. Exemplary non-transitory computer-readable mediums may include random access memory, read only memory, flash memory, and/or the like. Such non-transitory computer readable mediums may be electrically based, optically based, magnetically based, and/or the like.

As used herein, the term TTField (TTFields, or TTF(s)) refers to low intensity (e.g., 1-4 V/cm) alternating electric fields of medium frequencies (about 50 kHz-1 MHz, and more preferably from about 50 kHz-500 kHz) that when applied to a conductive medium, such as a human body, via electrodes may be used, for example, to treat tumors as described in U.S. Pat. Nos. 7,016,725, 7,089,054, 7,333,852, 7,565,205, 7,805,201, and 8,244,345 by Palti and in a publication by Kirson (see Eilon D. Kirson, et al., Disruption of Cancer Cell Replication by Alternating Electric Fields, Cancer Res. 2004 64:3288-3295). TTFields have been shown to have the capability to specifically affect cancer cells and serve, among other uses, for treating cancer. TTFields therapy is an approved mono-treatment for recurrent glioblastoma (GBM), and an approved combination therapy with chemotherapy for newly diagnosed GBM patients.

As used herein, the term TTSignal is an electrical signal that, when received by electrodes applied to a conductive medium, such as a human body, causes the electrodes to generate the TTField described above. The TTSignal is often an AC electrical signal.

Referring now to the drawings and in particular to FIG. 1, shown therein is an exemplary embodiment of a dividing cell 10, under the influence of external TTFields, generally indicated as lines 14, generated by a first electrode 18*a* having a negative charge and a second electrode 18*b* having a positive charge. Further shown are microtubules 22 that are known to have a very strong dipole moment. This strong polarization makes the microtubules 22, as well as other polar macromolecules and especially those that have a specific orientation within the cell 10 or its surroundings, susceptible to electric fields. The microtubules' 22 positive charges are located at two centrioles 26 while two sets of negative poles are at a center 30 of the dividing cell 10 and point of attachment 34 of the microtubules 22 to the cell membrane. The locations of the charges form sets of double dipoles and therefore are susceptible to electric fields of differing directions. In one embodiment, the cells go through electroporation, that is, DNA or chromosomes are introduced into the cells using a pulse of electricity to briefly open pores in the cell membranes.

Figure 2:
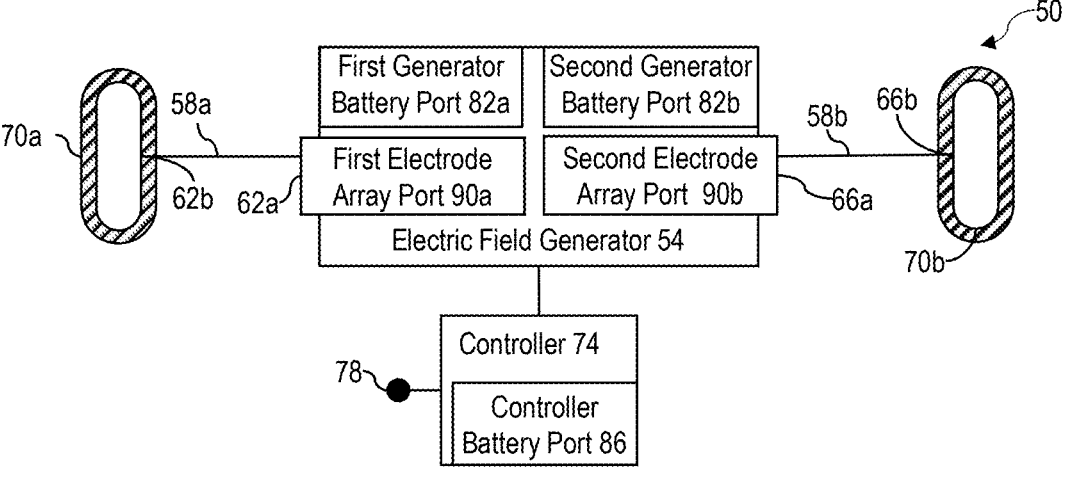
FIG. 2 is an exemplary embodiment of an electronic device configured to generate a TTField constructed in accordance with the present disclosure.

Turning now to FIG. 2, the TTFields described above that have been found to advantageously destroy tumor cells may be generated by an electronic apparatus 50. FIG. 2 is a simple schematic diagram of the electronic apparatus 50 illustrating major components thereof. The electronic apparatus 50 includes an electric field generator 54 and a pair of conductive leads 58, including first conductive lead 58a and second conductive lead 58b. The first conductive lead 58a includes a first end 62a and a second end 62b. The second conductive lead 58b includes a first end 66a and a second end 66b. The first end 62a of the first conductive lead 58a is conductively attached to a first electrode array port 90a of the electric field generator 54 and the first end 66a of the second conductive lead 58b is conductively attached to a second electrode array port 90b of the electric field generator 54.

The electric field generator 54 is configured to supply power to each electrode array port 90 and generates desirable electric signals (TTSignals) in the shape of waveforms or trains of pulses as an output. The second end 62b of the first conductive lead 58a is connected to an electrode array 70a and the second end 66b of the second conductive lead 58b is connected to an electrode array 70b. Both of the electrode array 70a and the electrode array 70b are activated by the electric signals (e.g., TTSignals, wave forms). The electrode array 70a and the electrode array 70b, being activated by the electric signals, cause an electrical current to flow between the electrode array 70a and the electrode array 70b. The electrical current generates an electric field (i.e., TTField), having a frequency and an amplitude, to be generated between the electrode array 70a and the electrode array 70b.

While the electronic apparatus 50 shown in FIG. 2 comprises only two electrode arrays 70 (i.e., the electrode array 70a and the electrode array 70b), in some embodiments, the electronic apparatus 50 may comprise more than two electrode arrays 70.

The electric field generator 54 generates an alternating voltage wave form (i.e., TTSignal) at frequencies in the range from about 50 kHz to about 1 MHz (preferably from about 100 kHz to about 500 kHz). The required voltages are such that an electric field intensity in tissue within the treatment area is in the range of about 0.1 V/cm to about 10V/cm. To achieve this electric field intensity, the potential difference between the two conductors (e.g., the electrode element 104 in FIG. 3) in each of the electrode array 70a or the electrode array 70b is determined by the relative impedances of the system components, e.g., a fraction of the electric field on each component is given by that component's impedance divided by a total circuit impedance.

In certain particular (but non-limiting) embodiments, the electrode array 70a and the electrode array 70b generate an alternating electric current and field within a target region of a patient. The target region typically comprises at least one tumor, and the generation of the alternating electric current and field selectively destroys and/or inhibits growth of the tumor. The alternating electric current and field may be generated at any frequency that selectively destroys or inhibits growth of the tumor, such as at any frequency of a TTField.

In certain particular (but non-limiting) embodiments, the alternating electric current and field may be imposed at two or more different frequencies. When two or more frequencies are present, each frequency is selected from any of the above-referenced values, or a range formed from any of the above-referenced values, or a range that combines two integers that fall between two of the above-referenced values.

In order to optimize the electric field (i.e., TTField) distribution, the electrode array 70a and the electrode array 70b (pair of transducer arrays) may be configured differently depending upon the application in which the pair of electrode arrays 70a and 70b are to be used. The pair of electrode arrays 70a and 70b, as described herein, are externally applied to a patient, that is, are generally applied to the patient's skin, in order to apply the electric current, and electric field (TTField) thereby generating current within the patient's tissue. Generally, the pair of electrode arrays 70a and 70b are placed on the patient's skin by a user such that the electric field is generated across patient tissue within a treatment area. TTFields that are applied externally can be of a local type or widely distributed type, for example, the treatment of skin tumors and treatment of lesions close to the skin surface.

In one embodiment, the user may be a medical professional, such as a doctor, nurse, therapist, or other person acting under the instruction of a doctor, nurse, or therapist. In another embodiment, the user may be the patient, that is, the patient (and/or a helper) may place the electrode array 70a and the electrode array 70b on the patient's treatment area.

According to another exemplary embodiment, the electronic apparatus 50 includes a controller 74 and, optionally, a temperature sensor 78 coupled to the controller 74.

In one embodiment, the controller 74 comprises circuitry configured to control the output of the electric field generator 54, for example, to set the output at the maximal value that does not cause excessive heating of the treatment area. The controller 74 may issue a warning, or the like, when a temperature of the treatment area (as sensed by temperature sensor 78) exceeds a preset limit. The temperature sensor 78 may be mechanically connected to and/or otherwise associated with the electrode array 70a and/or the electrode array 70b so as to sense the temperature of the treatment area at either one or both of the electrode array 70a or the electrode array 70b. In one embodiment, the controller 74 may turn off, or decrease power of the TTSignal generated by the electric field generator 54, if a temperature sensed by the temperature sensor 78 meets or exceeds a comfortability threshold. In one embodiment, the comfortability threshold is the temperature at which a patient would be made uncomfortable while using the electrode array 70a and the electrode array 70b. In one embodiment, the comfortability threshold is a temperature at or about 40 degrees Celsius. In one embodiment, the comfortability threshold is a temperature of between about 39 degrees Celsius and 42 degrees Celsius, or a specific selected temperature between about 39 degrees Celsius and 42 degrees Celsius, such as, for example, 41 degrees Celsius.

The conductive leads 58 are standard isolated conductors with a flexible metal shield, preferably grounded thereby preventing spread of any electric field generated by the conductive leads 58. The electrode array 70a and the electrode array 70b may have specific shapes and positioning so as to generate the TTField of a desired configuration, direction, and intensity at the treatment area and only at that treatment area so as to focus the treatment.

The specifications of the electronic apparatus 50 as a whole and its individual components are largely influenced by the fact that at the frequency of the TTFields, living systems behave according to their "Ohmic", rather than their dielectric properties.

In one embodiment, the electric field generator 54 further includes one or more generator battery port 82 (shown as 82*a* and 82*b* in FIG. 2) operable to receive or connect to a generator battery and electrically connect the generator battery to the electric field generator 54 to supply power to the electric field generator 54 as described in more detail below in relation to FIG. 4.

Additionally, in some embodiments, the controller 74 may include one or more controller battery port 86 operable to receive or connect to a controller battery 158 (FIG. 4) and electrically connect the controller battery 158 to the controller 74 as described below in more detail in relation to FIG. 4.

Figure 3:
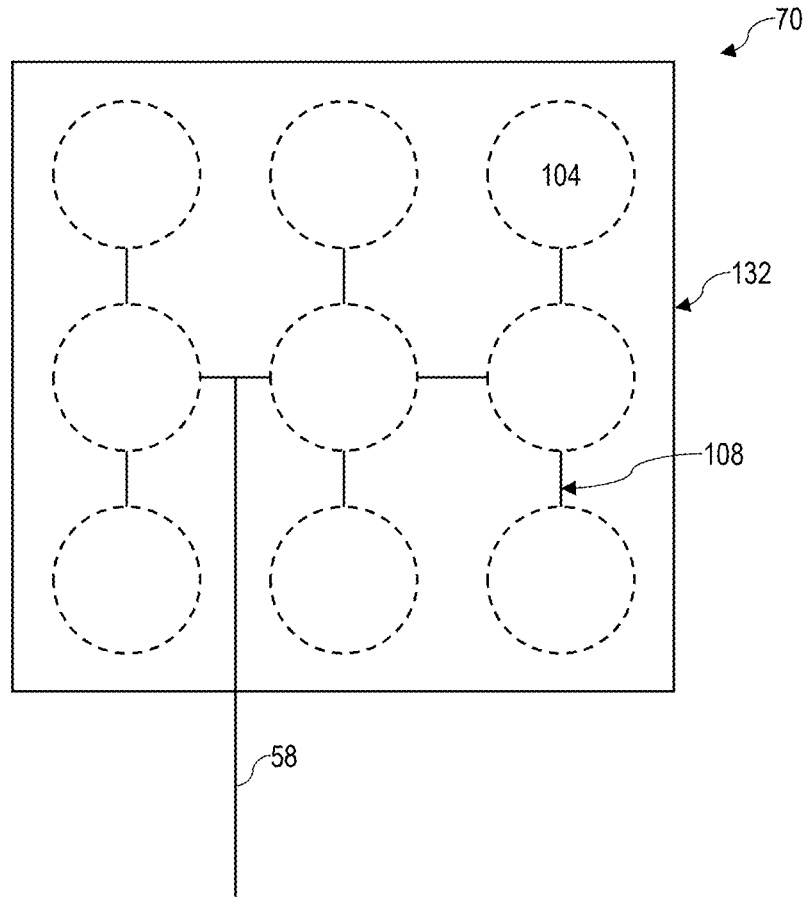
FIG. 3 is a block diagram of an exemplary embodiment of a transducer array constructed in accordance with the present disclosure.

Referring now to FIG. 3, shown therein is a diagram of an exemplary embodiment of the electrode array 70 constructed in accordance with the present disclosure. The electrode array 70 includes one or more electrode element 104. As shown in FIG. 3, each electrode array 70 is configured as a set of one or more electrode elements 104. Electrode arrays 70 may utilize electrode elements 104 that are capacitively coupled. In the example shown in FIG. 3, the electrode array 70 is configured as multiple electrode elements 104 (for example, about 2 cm in diameter) that are interconnected via flex wires 108 (and connected to the electric field generator via the conductive lead 58). Each electrode element 104 may include a dielectric layer (such as a ceramic disk or high-dielectric, thin-film polymer layer) and an electrode layer. In one embodiment, the electrode array 70 includes an outer peripheral edge 132.

Alternative constructions for the electrode array 70 may be used, including, for example ceramic elements that are disc-shaped, ceramic elements that are not disc-shaped, and non-ceramic dielectric materials positioned between the electrode layer and a skin-facing surface of the electrode arrays 70 over a plurality of flat conductors. Examples of non-ceramic dielectric materials positioned over a plurality of flat conductors include: polymer films disposed over electrical contacts on a printed circuit board or over flat pieces of metal. Electrode arrays 70 that utilize electrode elements 104 that are not capacitively coupled may also be used. In this situation, each electrode element 104 of the transducer array would be implemented using a region of a conductive material that is configured for placement against a patient's body, with no insulating dielectric layer disposed between the electrode elements 104 and the patient's body. Examples of the conductive material include a conductive film, a conductive fabric, and a conductive foam. Other alternative constructions for implementing the electrode arrays 70 may also be used, as long as they are capable of delivering TTFields to the patient's body. Optionally, a gel layer, e.g., a conductive gel layer, or a conductive adhesive layer may be disposed between the electrode array 70 and the patient's body in any of the embodiments described herein.

Figure 4:
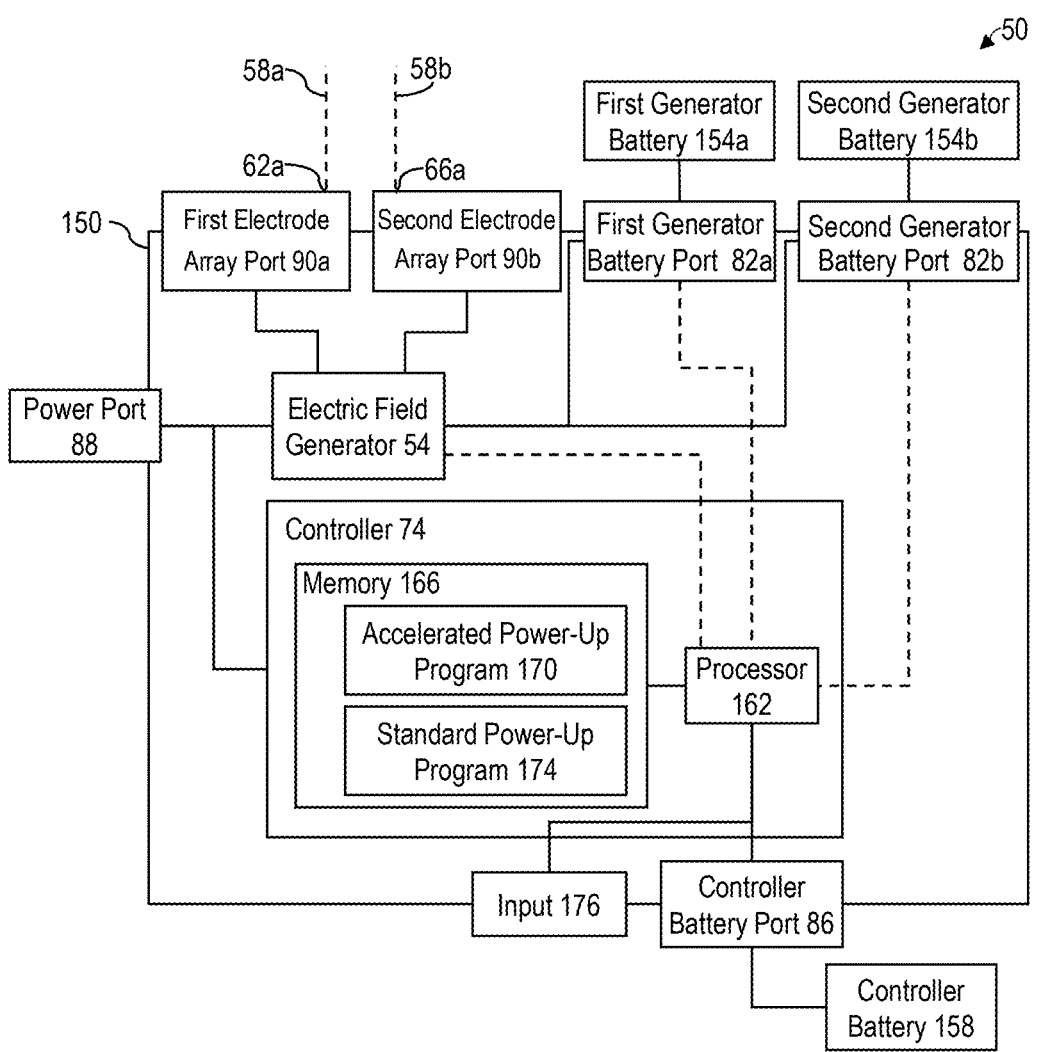
FIG. 4 is a block diagram of an exemplary embodiment of the electric field generator of FIG. 2 constructed in accordance with the present disclosure.

Referring now to FIG. 4, shown therein is a block diagram of an exemplary embodiment of the electronic apparatus 50 of FIG. 2 constructed in accordance with the present disclosure. As shown in FIG. 4, the electronic apparatus 50 generally comprises the electric field generator 54 supported by a housing 150. In some embodiments, the housing 150 may further support the controller 74. FIG. 4 further shows other features of FIG. 2, such as the first conductive lead 58*a* and second conductive lead 58*b*, each conductively attached, respectively, to the first electrode array port 90*a* and second electrode array port 90*b* of the electric field generator 54 via the first end 62*a* and 66*a* of the first conductive lead 58*a* and second conductive lead 58*b*, as described with respect to FIG. 2.

In one embodiment, one or more generator battery port 82 (e.g., 82*a* and 82*b*) operable to receive a generator battery 154 (e.g., 154*a* and 154*b*) is supported by the housing 150 and electrically coupled to the electric field generator 54. The generator battery port 82 may be separate from and supported by the housing 150 or may be integrally and/or partially formed within the housing 150.

In one embodiment, the electronic apparatus 50 includes a first generator battery port 82*a* and an optional second generator battery port 82*b*, as depicted in FIG. 4. In this embodiment, each of the first generator battery port 82*a* and the second generator battery port 82*b* may independently supply power to the electric field generator 54. In some embodiments, the first generator battery port 82*a* may be associated with a first generator battery 154*a* and the second generator battery port 82*b* may be associated with a second generator battery 154*b*.

In one embodiment, the electronic apparatus 50 includes a controller battery port 86 coupled to the processor 162 via circuitry so as to supply power to the processor 162, and other components of the controller 74 such as the memory 166, independent of any power supplied to the first generator battery port 82*a* and/or optional second generator battery port 82*b*.

In one embodiment, the electronic apparatus 50 further includes a controller charging circuitry operable to charge the controller battery 158. In some embodiments, the controller battery 158 may be charged from one or more of the first generator battery 154*a* and the second generator battery 154*b*. In some embodiments, the controller battery 158 may be charged via a power port 88.

In one embodiment, the electronic apparatus 50 further includes the power port 88. The power port 88 may be separate from, and supported by, the housing 150 or may be integrally and/or partially formed within the housing 150. The power port 88 may be operable to supply power to the electrical field generator 54 and/or the controller 74 independent of any generator battery 154 and/or controller battery 158. In some embodiments, the electronic apparatus 50, receiving power from the power port 88, may include circuitry operable to charge the generator battery 154 and/or the controller battery 158.

In one embodiment, the controller 74 may further comprise circuitry to interface with the generator battery ports 82 and the controller battery port 86. The circuitry may include, for example, a processor 162 in communication with a non-transitory computer-readable medium (e.g., a memory 166). The memory 166 may store computer-executable instructions that when executed by the processor 162 causes the processor 162 to perform one or more action, as described below for example. In one embodiment, the controller 74 is integrated with the electric field generator 54.

In some embodiments, the first generator battery 154*a* may be characterized as a primary battery and the second generator battery 154*b* may be characterized as a backup battery. In these embodiments, the controller 74 is configured to maintain the TTFields being delivered to the patient during a battery change. In these embodiments, the first generator battery 154*a* has a much larger capacity than the second generator battery 154*b*. For example, the first generator battery 154*a* may be a 100 W, 30V battery with a first charge capacity of about 3,000 mAh, while the second generator battery 154*b* (e.g., the backup battery) may be a 30V battery with a second charge capacity of about 300 mAh. In some embodiments, the first generator battery 154*a* provides between 20 Wh and 30 Wh to the electric field generator 54 for a duration of between 3 and 4 hours.

In one embodiment, the first generator battery 154*a* is configured to supply continuous power to the electric field generator 54 for a significant period of time, such as a time period between 30 minutes and 300 minutes. The second generator battery 154*b* is configured to supply continuous power to the electric field generator 54 for a much smaller period of time, such as a time period between 1 minute and 10 minutes. In these embodiments, the circuitry of the electronic apparatus 50 can be configured to permit the first generator battery 154*a* to supply continuous power until a charge capacity of the first generator battery 154*a* is at or below a predetermined power level. Upon determining that the first generator battery 154*a* is at or below the predetermined power level, the processor 162 provides a signal to a user to change the first generator battery 154*a*, and then also provides a signal to the electric field generator 54 to begin drawing power from the second generator battery 154*b*. The second generator battery 154*b* provides power to the electric field generator 54 during a period when the first generator battery 154*a* is disconnected from the first generator battery port 82*a*, i.e., is being changed, thereby providing continuous power to the electric field generator 54 and avoiding the occurrence of the traditional initialization procedure discussed above. Upon completion of the change and installation of a replacement first generator battery 154*a* (i.e., the change has occurred and the replacement generator battery is connected to the first generator battery port 82*a*), a signal is provided to the electric field generator 54 to begin drawing power from the (replacement) first generator battery 154*a*, and begin charging the second generator battery 154*b* in anticipation of another power change in the future. In one embodiment, the second generator battery 154*b* has a charge of ⅓ to ⅓₀₀ of the charge capacity of the first generator battery 154*a* and more preferably within a range of ⅕ to ⅓₀₀, such as, for example, ¹⁄₁₀, of the charge capacity of the first generator battery 154*a*. In one embodiment, the replacement first generator battery 154*a* may be referred to as a replacement battery, or a replacement generator battery.

In one embodiment, the processor 162, in communication with each of the first generator battery port 82*a* and the second generator battery port 82*b*, may determine or detect a presence of and/or a present capacity of the first generator battery 154*a* and/or the second generator battery 154*b*. Additionally, the processor 162, in communication with the controller battery port 86 may determine or detect a presence of and/or a present capacity of the controller battery 158.

In one embodiment, the processor 162, in communication with each generator battery port 82 (e.g., the first generator battery port 82*a* and the second generator battery port 82*b*), may detect insertion and/or new connection of a generator battery 154 to the generator battery port 82 and, in response to the detection, trigger a generator battery change event. For example, if a generator battery 154 is newly connected to or inserted into the second generator battery port 82*b*, the processor 162 of the controller 74 may detect the insertion of the generator battery 154 and, in response, trigger the generator battery change event.

In one embodiment, the processor 162, in communication with each generator battery port 82 (e.g., the first generator battery port 82*a* and the second generator battery port 82*b*), may monitor and detect removal and/or disconnection of a generator battery 154 to the generator battery port 82 and, in response to the detection, trigger a generator power-down event. For example, if a generator battery 154 is disconnected from or removed from the first generator battery port 82*a* and/or the second generator battery port 82*b*, the processor 162 of the controller 74 may detect the removal of the generator battery 154 and, in response, trigger the generator power-down event. Alternatively, in an embodiment, the processor 162 of the controller 74 may be programmed to trigger the generator power-down event only if the first generator battery 154*a* is disconnected from or removed from the first generator battery port 82*a*. In an embodiment, if only the second generator battery 154*b* is disconnected from or removed from the second generator battery port 82*b* then the processor 162 of the controller 74 may be programmed to generate a warning signal indicating such event.

In one embodiment, the processor 162, in communication with each generator battery port 82 (e.g., the first generator battery port 82*a* and the second generator battery port 82*b*), may detect a battery charge, or charge capacity, for the generator battery 154 connected to the generator battery port 82. The battery charge may be, for example, a battery capacity, such as in milliAmpere Hours (mAh) or may be in percentage such as a percent remaining of the battery charge. In some embodiments, the processor 162 may compare a charge capacity of a connected generator battery 154 to a minimum operating capacity, and, if the charge capacity is less than (or about equal to) the minimum operating capacity, the processor 162 may generate a signal indicative of the generator battery having the charge capacity below the minimum operating capacity.

In one embodiment, the minimum operating capacity is a minimum charge capacity a battery must have in order for the controller 74 to cause the electrical field generator 54 to actuate. For example, if the generator battery 154 connected to the generator battery ports 82 does not have enough charge to power the electrical field generator 54 for a predetermined duration, the processor 162 may generate a signal indicating as much. The user, once notified that the generator battery 154 is not charged enough to power the electrical field generator 54, may be instructed to, for example, change the generator battery 154 and/or place the generator battery 154 on a charger.

The processor 162 may also be in communication with the electric field generator 54. The processor 162 may actuate the electric field generator 54 thereby causing the electric field generator 54 to transmit a TTSignal at a predetermined power for a predetermined period of time. For example, the processor 162 may cause the electric field generator 54 to transmit the TTSignal at a first initial power and thereafter increase the first initial power to an operating power over a predetermined period of time, e.g., a ramp-up period of time. The processor 162 may further cause the electric field generator 54 to transmit the TTSignal at a first initial voltage or first initial current and thereafter increase the first initial voltage or the first initial current to an operating voltage or an operating current over a predetermined period of time, e.g., a ramp-up period of time. The processor 162 may further deactuate the electric field generator 54 so as to cause the electric field generator 54 to cease transmitting the TTSignal.

The processor 162, in communication with the electric field generator 54, may store one or more operating parameter of the electric field generator 54 in the memory 166, for example, in response to a generator power-down event. The one or more operating parameter is data indicative of an operation of the electric field generator 54 or cessation of operation of the electric field generator 54. For example, the operating parameter may be a calculation or measurement of an output of the electric field generator 54, one or more of a power of the TTSignal being transmitted by the electric field generator 54 immediately preceeding deactuation, a timestamp indicative of a time at which the electric field generator 54 is actuated and/or deactuated, a deactivation duration, a circuit resistance, a voltage of the TTSignal being transmitted by the electrical field generator 54 prior to deactuation, a power of the TTSignal being transmitted by the electrical field generator 54 prior to deactuation, and/or the like.

Additionally, in some embodiments, the processor 162 may store one or more operating parameter indicative of a battery property of each of the generator battery 154 and/or the controller battery 158 in the memory 166. The one or more battery property may include a battery charge level of each generator battery 154, a battery charge level of the controller battery 158, a timestamp indicative of a time at which the generator battery 154 was installed or fully charged, a time stamp indicative of a time at which the controller battery 158 was installed or fully charged, a cycle count for the generator battery 154 and/or the controller battery 158, and/or the like. The processor can be configured to store such data (operating parameters) continually, both before and after the generator power-down event.

In one embodiment, the controller 74 may store an accelerated power-up program 170 and a standard power-up program 174 in the memory 166. The standard power-up program 174, when executed, causes the processor 162 to perform a standard initialization procedure in which the TTField supplied to the patient is initially low and then ramps up slowly over a relatively large period of time such as 30 minutes. The accelerated power-up program 170 stored in the memory 166 may include computer-executable instructions that when executed by the processor 162 causes the processor 162 to perform an accelerated power-up process in which the TTField supplied to the patient is either at the operating power or within 10% of the operating power as explained below. The standard power-up program 174 may be used to initiate the TTField supplied to the patient (as a safety measure) when one or more operating parameter provided to the processor 162 indicate that the electrode arrays 70 (FIG. 2) may have been tampered with or recently applied to the patient. The accelerated power-up program 170 may be used to initiate the TTField supplied to the patient at a higher power level to provide a higher level of treatment to the patient when one or more operating parameter provided to the processor 162 indicate that it is safe to do so, e.g., when the one or more operating parameter indicate that the electrode arrays 70 have not been tampered with or newly applied.

In one embodiment, the electronic apparatus 50 includes one or more input 176 integrated with and/or at least partially supported by the housing 150. The processor 162 may detect one or more interaction with the input 176 (i.e., an input related to a battery change or a generator power down event) and, upon detecting an interaction indicative of an intent to turn off the electric field generator 54 or change the generator battery 154, may trigger a generator power-down event. The generator power-down event is a physical interaction with the input 176 of the electronic apparatus 50 that indicates that the electric field generator 54 should be powered down. The intent to turn off the electric field generator 54 may be an intent by a user or pre-programmed based upon certain conditions provided to the input 176. The input 176 may be, for example, a button indicating an intention to perform a battery change, a power button for the electronic apparatus 50, a sensor monitoring disconnection of a pin of the generator battery port 82, a sensor monitoring a charge capacity of the generator battery 154, and/or a sensor monitoring another aspect of the electronic apparatus 50 that may indicate that the electrical field generator 54 is to be powered-down.

Figure 5:
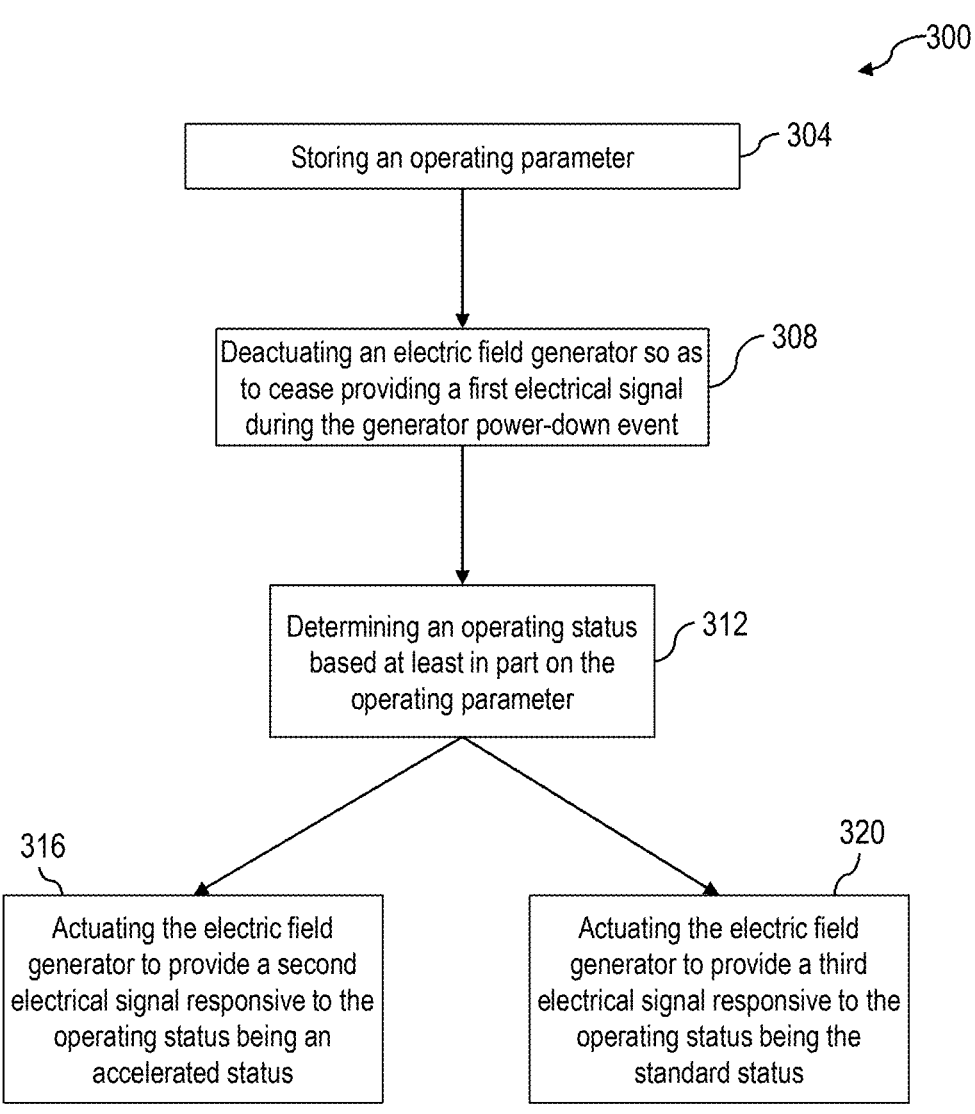
FIG. 5 is a process flow diagram of an exemplary embodiment of a battery exchange process in accordance with the present disclosure.

Referring now to FIG. 5, shown therein is a process flow diagram of an exemplary embodiment of an exchange process 300 in accordance with the present disclosure. The exchange process 300 generally comprises the steps of: storing an operating parameter indicative of an operation of the electric field generator or cessation of operation of the electric field generator (step 304); deactuating an electric field generator so as to cease providing a first electrical signal during the generator power-down event (step 308); determining an operating status based at least in part on the operating parameter (step 312); actuating the electric field generator to provide: i) a second electrical signal responsive to the operating status being an accelerated status (step 316); or ii) a third electrical signal responsive to the operating status being the standard status (step 320). Generally, by storing the operating parameter in response to the generator power-down event, the exchange process 300 provides for determining whether one or more electrode array 70 has been tampered with, and, if the one or more electrode array 70 has been tampered with, causing the processor 162 to execute the standard power-up program 174, but if the one or more electrode array 70 has not been tampered with, causing the processor 162 to execute the accelerated power-up program 170.

In one embodiment, storing an operating parameter indicative of an operation of the electric field generator or cessation of operation of the electric field generator (step 304) may occur in response to a generator power-down event and includes receiving, e.g., by the processor 162, the generator power-down event and storing, e.g., in the memory 166, one or more operating parameter.

In one embodiment, storing an operating parameter indicative of an operation of the electric field generator or cessation of operation of the electric field generator (step 304) includes storing the operating parameter wherein the operating parameter is a data indicative of a circuit resistance. The data of the operating parameter may be determined prior to deactuating the electric field generator (step 308). By storing the data indicative of the circuit resistance, the circuit resistance may be compared to a second circuit resistance measured prior to actuating the electric field generator in order to determine whether the electrode arrays 70 have been tampered with while the generator battery 154 is being exchanged.

In one embodiment, storing an operating parameter indicative of an operation of the electric field generator or cessation of operation of the electric field generator (step 304) includes storing the operating parameter wherein the operating parameter is a data indicative of one or more electric field property (i.e., TTField property). For example, the operating parameter may be indicative of a present power of the first electrical signal (e.g., a power of the TTSignal when the operating parameter is stored), a voltage of the first electrical signal, a frequency of the first electrical signal, and a current of the first electrical signal. Each of the data of the operating parameter may be determined prior to deactuating the electric field generator (step 308). The operating parameter indicative of the power, the voltage, the current, and/or the frequency of the first alternating current waveform may be utilized by the accelerated power-up program 170 to determine a second initial power, a second initial voltage, a second initial current, and/or a second initial frequency of a second alternating current waveform (for the accelerated power-up process), as described below in more detail.

In one embodiment, the operating parameter is one or more of a first timestamp indicative of a time at which a generator battery 154 is removed from the generator battery port 82, a second timestamp indicative of a time at which the generator battery no longer has a charge sufficient to operate the electric field generator 54, and/or an initiation of an exchange timer (the starting point in measuring the duration of time that the electric field generator 54 is deactuated). Each of the first timestamp, the second timestamp, and the exchange timer may be used by the processor 162 to measure a deactivation duration of the electric field generator 54. By measuring the deactivation duration, the processor 162 may determine whether tampering with one or more electrode array 70 is likely to have occurred, thus resulting in standard status, or whether tampering with the one or more electrode array 70 is not likely to have occurred, thus potentially resulting in an operating status being the accelerated status. In other words, the standard status is an operating status indicative of a determination that the standard power-up program should be executed and the accelerated status is an operation status indicative of a determination that the accelerated power-up program should be executed.

In one embodiment, storing an operating parameter in response to a generator power-down event (step 304) includes receiving, e.g., by the processor 162, the generator power-down event triggered by one or more of a low battery capacity of the generator battery, a removal of the generator battery, an insertion of a second generator battery, a disconnection of the electric field generator from main power, and/or the like.

For example, in one embodiment, the processor 162 may monitor one or more generator battery port 82 to detect removal of a first generator battery, and upon detection of removal of the first generator battery, the processor 162 may trigger a generator power-down event. Similarly, the processor 162 may monitor the power port 88 to detect removal of a power source attached to the power port 88, such as removal or disconnection of a main, or wall, power, and upon detection of removal of the power source attached to the power port 88, trigger the generator power-down event. In one embodiment, interaction with the input 176 may trigger the generator power-down event.

In another example, the processor 162 may monitor one or more generator battery port 82 to detect a battery level of a first generator battery connected to the generator battery port 82 of the electrical field generator 54, and, if the first generator battery has a charge capacity below a minimum operating capacity, the processor 162 generates a signal indicative of the first generator battery having a charge capacity below the minimum operating capacity. In one embodiment, the signal may include triggering a generator power-down event. The minimum operating capacity may be, for example, set at about 5-15% of a maximum charge of the first generator battery (e.g., generator battery 154). In one embodiment, the signal may be sent to the user, a helper, or a medical professional. The signal may activate, for example, a visual feedback device such as an LED, LCD, a haptic feedback device, an audio feedback device such as a speaker, a notification on a smart phone, an app, a website, an email, a text message (e.g., SMS, MMS, etc.), and/or the like. In one embodiment, the battery level may be a percent charge remaining, a voltage of a battery (e.g., the first generator battery), an amp-hours available or remaining, and/or the like.

In one embodiment, storing an operating parameter (step 304) includes monitoring one or more electric field property (i.e., TT Signal property, or TTField property) and, then storing data indicative of the operating parameter. Monitoring and storing the one or more electric field property can be accomplished periodically or in response to a specific input, such as in response to the generator power-down event. The operating parameter can be data indicative of the one or more electric field property prior to the generator power-down event. For example, the operating parameter may be indicative of a power of the first electrical signal (e.g., a power of the TTSignal prior to receiving the generator power-down event), a voltage of the first electrical signal, a frequency of the first electrical signal, and a current of the first electrical signal. Each of the data of the operating parameter may be determined prior to deactuating the electric field generator (step 308). The operating parameter indicative of the power, the voltage, the current, and/or the frequency of the first alternating current waveform may be utilized by the accelerated power-up program 170 to determine a second initial power, a second initial voltage, a second initial current, and/or a second initial frequency of a second alternating current waveform (for the accelerated power-up process), as described below in more detail. Furthermore, the monitoring may extend during the standard power-up process and/or the accelerated power-up process. For example, the circuit resistance can be measured during the accelerated power-up process (or the standard power-up process) such that if the user moves an array after the accelerated power-up process (or the standard power-up process) has started, the controller 74 ceases the accelerated power-up process (or the standard power-up process) and reverts to starting the standard power-up process. In one embodiment, the processor 162 may monitor the one or more electric field property periodically, e.g., may monitor the one or more electric field property at a first time and, after a wait time, monitor the one or more electric field property a second time. In some embodiments, the processor 162 may monitor the one or more electric field property continuously, e.g., the processor 162 may have a set of instructions for reading the one or more electric field that are repeated until being interrupted.

In one embodiment, deactuating an electric field generator so as to cease providing a first electrical signal during the generator power-down event (step 308) includes sending a control signal, e.g., from the processor 162, to the electrical field generator 54 to cause the electrical field generator 54 to cease providing the first electrical signal to each electrode array 70.

In one embodiment, determining an operating status based at least in part on the operating parameter (step 312) includes determining, by the processor 164, the operating status which may be one of an accelerated status and a standard status. While in some embodiments, the operating status is only one of the accelerated status and the standard status, in other embodiments, the operating status may include one or more additional status. The operating status may be determined to be the standard status when potential tampering with the electrode arrays is detected whereas the operating status may be determined to be the accelerated status when no potential tampering with the electrode arrays is detected.

In one embodiment, determining an operating status based at least in part on the operating parameter (step 312)

includes determining the operating status after detecting installation of a replacement first generator battery 154*a* prior to actuating the electric field generator 54. Generally, once the first generator battery 154*a* is replaced with the replacement first generator battery operable to supply power to the electric field generator 54, the processor 162 determines an operating status in order to determine whether to execute one of either the accelerated power-up program 170 when the operating status is the accelerated status or the standard power-up program 174 when the operating status is the standard status.

In one embodiment, determining an operating status based at least in part on the operating parameter (step 312) includes determining the operating status periodically or continuously between triggering of the generator power-down event and actuating the electrical field generator to provide the second electrical signal (step 316). In one embodiment, the operating status may be determined multiple times a second prior to actuating the electrical field generator to provide the second electrical signal (step 316) or the third electrical signal (step 320). For example, the processor 162 in communication with the electrode array ports 90, may detect and monitor the circuit resistance between the electrode arrays 70 (e.g., as a monitored circuit resistance) and if the monitored circuit resistance exceeds a resistance threshold, e.g., is above a predetermined resistance or is below a predetermined resistance) the processor 162 may determine that the operating status is the standard status.

In one embodiment, determining an operating status based at least in part on the operating parameter (step 312) includes determining, by the processor 164, the operating status is the accelerated status if a deactivation duration is below a predetermined deactivation duration threshold, or to be the standard status if the deactivation duration exceeds the predetermined deactivation duration threshold. For example, if the operating parameter includes a power-down event timestamp, such as a time at which the processor 162 received the generator power-down event, the deactivation duration may be determined by comparing a present time-stamp to the power-down event timestamp. The predetermined deactivation duration threshold may be, for example, about 2 minutes (or about 120 seconds), or about 5 minutes, or in a range of about 2 minutes to about 5 minutes. Thus, in this example, determining an operating status based at least in part on the operating parameter (step 312) includes determining, by the processor 164, the operating status is the accelerated status if the deactivation duration is less than 2 minutes (or less than 5 minutes) and that the operating status is the standard status if the deactivation duration is greater than 2 minutes (or greater than 5 minutes). In some embodiments, the predetermined deactivation duration threshold is set by the user (and/or a helper), or a medical professional, whereas in other embodiments, the predetermined deactivation duration threshold is set by a manufacturer.

In one embodiment, determining an operating status based at least in part on the operating parameter (step 312) includes monitoring disconnection of at least one electrode array 70 from an electrode array port 90, and, upon detection of a disconnection of any electrode array 70 from the electrode array port 90, determining that the operating status is the standard status. In some embodiments, a disconnection of any electrode array 70 results in the operating status being the standard status, while a lack of disconnection of all electrode arrays 70 does not necessarily result in the operating status being the accelerated status.

In one embodiment, the operating status is assumed to be the accelerated status until the operating status is changed to the standard status. In other embodiments, the operating status is assumed to be the standard status until the operating status is changed to the accelerated status. In some embodiments, if the operating status is defaulted to the accelerated status, any change of the operating status to the standard status prevents the operating status from changing back to the accelerated status until the exchange process 300 is complete; however, if the operating status is defaulted to the standard status, any change of the operating status to the accelerated status may be reverted to the standard status. In other words, in some embodiments, any condition that results in the operating status being set to the standard status results in the processor 162 executing the standard power-up program 174.

In one embodiment, actuating the electric field generator to provide a second electrical signal responsive to the operating status being an accelerated status (step 316) includes providing the second electrical signal having a second alternating current waveform at a frequency in the range from 50 kHz to 1 MHz. The processor 162 may execute the accelerated power-up program 170 stored in the memory 166 thereby actuating the electric field generator 54 to provide the second electrical signal responsive to the operating status being the accelerated status.

In one embodiment, actuating the electric field generator to provide a second electrical signal responsive to the operating status being an accelerated status (step 316) includes actuating the electrical field generator to provide the second electrical signal having the second alternating current waveform with a second power greater than a third power of the third electrical signal. In other words, the second alternating current waveform resulting from executing the accelerated power-up program has the second power being greater than the third power of the third alternating current waveform resulting from executing the standard power-up program.

In one embodiment, actuating the electric field generator to provide a second electrical signal responsive to the operating status being an accelerated status (step 316) includes actuating the electrical field generator to provide the second electrical signal having the second alternating current waveform with a second initial power.

In one embodiment, actuating the electric field generator to provide a second electrical signal responsive to the operating status being an accelerated status (step 316) includes actuating the electrical field generator, e.g., by transmission of a control signal from the processor 162 to the electrical field generator 54, to provide the second electrical signal having the second alternating current waveform with a second initial power of between an operating power and 95% of the operating power. The operating power may be determined, for example, by the operating parameter having the data indicative of the power of the first alternating current waveform (i.e., the power of the TTSignal prior to the generator power-down event).

In one embodiment, prior to actuating the electric field generator to provide a second electrical signal responsive to the operating status being an accelerated status (step 316), an amount of charge of a first battery may be compared against an amount of charge of a second battery, e.g., by the processor 162. In one embodiment, if the amount of charge of the second battery is within 5-15% of the amount of charge of the first battery, then actuating the electric field generator to provide the second electrical signal (step 316) may not be executed. In some embodiments, if the amount of charge of the second battery is within 5-15% of the amount of charge of the first battery, then the processor 162 may set operating status to a warning status.

In one embodiment, actuating the electric field generator to provide a second electrical signal responsive to the operating status being an accelerated status (step 316) includes actuating the electric field generator to provide the second electrical signal based upon the operating parameter having the data indicative of either the voltage or the current of the first alternating current waveform, wherein either a second initial voltage of the second alternating current waveform or a second current of the second alternating current waveform is selected such that a second power of the second alternating current waveform is between a power of the first alternating current waveform and 95% of the power of the first alternating current waveform.

In one embodiment, actuating the electric field generator to provide a second electrical signal responsive to the operating status being an accelerated status (step 316) includes providing a first ramp-up time lesser than a second ramp-up time provided when actuating the electric field generator to provide the third electrical signal responsive to the operating status being the standard status. For example, responsive to the operating status being the accelerated status, the second electrical signal may have the second alternating current waveform with a second initial voltage or second initial current set to the first initial voltage or the first initial current and increase the second initial voltage and/or the second initial current to the operating voltage and/or the operating current over a shorter period of time than when actuating the electric field generator to provide the third electrical signal responsive to the operating status being the standard status. In some embodiments, the first ramp-up time is between 10 minutes and 30 minutes.

In one embodiment, the ramp-up time is determined based on a location of the electrode arrays 70 on the patient. For example, the ramp-up time may be shorter for electrode arrays 70 placed on the patient's head than the ramp-up time for electrode arrays 70 placed on the patient's torso. In one embodiment, the ramp-up time may be calculated based on the first power, the operating power, and a ramp-up rate. For example, if the electric field applied to the patient's head has a first operating power and the electric field applied to the patient's torso has a second operating power less than the first operating power, then the ramp-up time for the electric field applied to the patient's head is less than the ramp-up time for the electric field applied to the patient's torso for the same ramp-up rate.

In one embodiment, actuating the electric field generator to provide a third electrical signal responsive to the operating status being the standard status (step 320), includes actuating the electric field generator responsive to the operating status being the standard status wherein the third electrical signal has a third alternating current waveform at a frequency in the range of 50 kHz to 1 MHz. The processor 162 may actuate the electrical field generator 54 to provide the third electrical signal responsive to the operating status being the standard status. In one embodiment, the processor 162 may retrieve the operating status from the memory 166.

In one embodiment, actuating the electric field generator to provide a third electrical signal responsive to the operating status being the standard status (step 320), includes actuating the electric field generator responsive to the operating status being the standard status wherein the third electrical signal has a third initial power. In some embodiments, the third initial power is equal to the first initial power. In other embodiments, the third initial power is within 10% of the first initial power.

ILLUSTRATIVE EMBODIMENTS

The following is a non-limiting list of illustrative embodiments of the inventive concepts disclosed herein:

Illustrative Embodiment 1. An electronic apparatus, comprising:

an electric field generator configured to provide a first electrical signal having a first alternating current waveform at a frequency in a range from 50 kHz to 1 MHz; and a controller communicating with the electric field generator to control an output of the electric field generator, the controller having an input, a processor and a non-transitory computer-readable medium storing an accelerated power-up program, a standard power-up program, and computer-executable instructions that when executed by the processor cause the processor to:

receive a generator power-down event by the input, the generator power-down event being a physical interaction with the input;

detect the generator power-down event;

deactuate the electric field generator so as to cease providing the first electrical signal; store an operating parameter indicative of an operation of the electric field generator or cessation of operation of the electric field generator;

determine an operating status based at least in part on the operating parameter, the operating status being one of an accelerated status and a standard status; and actuate the electric field generator to provide:

i) a second electrical signal using the accelerated power-up program responsive to the operating status being the accelerated status; the second electrical signal having a second alternating current waveform at a frequency in the range from 50 kHz to 1 MHz; or ii) a third electrical signal with the standard power-up program responsive to the operating status being the standard status, the third electrical signal having a third alternating current waveform at a frequency in the range from 50 kHz to 1 MHz.

Illustrative Embodiment 2. The electronic apparatus of Illustrative Embodiment 1, wherein the electric field generator further comprises at least one electrode array port and is further configured to supply power to the at least one electrode array port.

Illustrative Embodiment 3. The electronic apparatus of any of Illustrative Embodiments 1-2, wherein the generator power-down event includes a generator battery change event that is triggered by one or more of removal of a first generator battery and insertion of a second generator battery.

Illustrative Embodiment 4. The electronic apparatus of any of Illustrative Embodiments 1-3, wherein the computer-executable instructions further comprise instructions that when executed by the processor cause the processor to detect a battery level of a first generator battery connected to the electric field generator, and, if the first generator battery has a charge capacity below a minimum operating capacity, to generate a signal indicative of the first generator battery having a charge capacity below the minimum operating capacity.

Illustrative Embodiment 5. The electronic apparatus of Illustrative Embodiment 4, wherein the processor includes computer-executable instructions that when executed by the processor cause the processor to receive the signal indicative of the first generator battery having the charge capacity below the minimum operating capacity and to trigger the generator power-down event.

Illustrative Embodiment 6. The electronic apparatus of any of Illustrative Embodiments 1-5, wherein the computer-executable instructions further comprise instructions that when executed by the processor cause the processor to store the operating parameter indicative of a deactivation duration of the electric field generator, and wherein determining the operating status includes determining the operating status is the accelerated status if the deactivation duration is below a predetermined deactivation duration threshold.

Illustrative Embodiment 7. The electronic apparatus of Illustrative Embodiment 6, wherein the predetermined deactivation duration threshold is 5 minutes.

Illustrative Embodiment 8. The electronic apparatus of any of Illustrative Embodiments 1-7, wherein:

the accelerated power-up program includes computer-executable instructions that when executed by the processor cause the processor to transmit a first control signal to the electric field generator to cause the electric field generator to increase a power of the second alternating current waveform to an operating power over a first time period; and the standard power-up program includes computer-executable instructions that when executed by the processor cause the processor to transmit a second control signal to the electric field generator to cause the electric field generator to increase a power of the third alternating current waveform to the operating power over a second time period; and wherein, the first time period is less than the second time period.

Illustrative Embodiment 9. The electronic apparatus of any of Illustrative Embodiments 1-8, wherein the standard power-up program includes computer-executable instructions that when executed by the processor cause the processor to transmit a control signal to the electric field generator to cause the electric field generator to set an initial power of the third alternating current waveform to less than 95% of an operating power.

Illustrative Embodiment 10. The electronic apparatus of any of Illustrative Embodiments 1-9, wherein the accelerated power-up program includes computer-executable instructions that when executed by the processor cause the processor to transmit a control signal to the electric field generator to cause the electric field generator to set a power of the second alternating current waveform to between an operating power and 95% of the operating power, inclusive.

Illustrative Embodiment 11. The electronic apparatus of any of Illustrative Embodiments 1-10, wherein the electric field generator is connected to a first electrode array and a second electrode array, and wherein the computer-executable instructions further comprise instructions that when executed by the processor cause the processor to monitor disconnection of at least one of the first electrode array and the second electrode array wherein, upon detection of a disconnection of at least one of the first electrode array and the second electrode array, the operating status is set to the standard status.

Illustrative Embodiment 12. The electronic apparatus of any of Illustrative Embodiments 1-11, wherein the electric field generator is connected to a first electrode array and a second electrode array, and wherein the computer-executable instructions further comprise instructions that when executed by the processor cause the processor to monitor disconnection of at least one of the first electrode array and the second electrode array and to generate a warning signal indicative of a disconnection of at least one of the first electrode array and the second electrode array.

Illustrative Embodiment 13. The electronic apparatus of any of Illustrative Embodiments 1-13, further comprising:

a first electrode array; and a second electrode array; and wherein the electric field generator is connected to the first electrode array and the second electrode array, and wherein the computer-executable instructions further comprise instructions that when executed by the processor cause the processor to:

store a measurement of circuit resistance as the operating parameter; and monitor a circuit resistance during a period of time in which the electric field generator is deactuated.

Illustrative Embodiment 14. The electronic apparatus of Illustrative Embodiment 13, wherein if the monitored circuit resistance differs from the circuit resistance stored as the operating parameter by more than a resistance threshold, the operating status is set to the standard status.

Illustrative Embodiment 15. The electronic apparatus of any of Illustrative Embodiments 1-14, wherein the accelerated power-up program further includes computer-executable instructions that when executed by the processor cause the processor to actuate the electric field generator to provide the second electrical signal having the second alternating current waveform with the frequency of the first alternating current waveform.

Illustrative Embodiment 16. An electronic apparatus, comprising:

an electric field generator having a housing and first circuitry positioned within the housing, the first circuitry operable to generate an electrical signal having an alternating current waveform at a frequency in a range from 50 kHz to 1 MHz, the housing having a first generator battery port and a second generator battery port independent of the first generator battery port, the first generator battery port and the second generator battery port coupled to the first circuitry so as to independently supply power to the first circuitry; and a controller communicating with the electric field generator to control an output of the electric field generator, the controller having a processor coupled to a controller battery port, the controller battery port coupled to the processor with a second circuitry so as to supply power to the processor independent of any power supplied to the first generator battery port and the second generator battery port.

Illustrative Embodiment 17. The electronic apparatus of Illustrative Embodiment 16, further comprising:

a first generator battery coupled to the first generator battery port, the first generator battery having a first amount of charge; and a second generator battery coupled to the second generator battery port, the second generator battery having a second amount of charge within a range of $\frac{1}{3}$ to $\frac{1}{300}$ of the first amount of charge.

Illustrative Embodiment 18. A method, comprising:

storing an operating parameter, the operating parameter being indicative of an operation of an electric field generator or cessation of operation of the electric field generator, the electric field generator configured to provide a first electrical signal having a first alternating current waveform at a frequency in a range from 50 kHz to 1 MHz;

deactuating the electric field generator so as to cease providing a first electrical signal;

determining an operating status based at least in part on the operating parameter, the operating status being one of an accelerated status and a standard status;

actuating the electric field generator to provide:

i) a second electrical signal responsive to the operating status being an accelerated status, the second electrical signal having a second alternating current waveform at a frequency in the range from 50 kHz to 1 MHz; or ii) a third electrical signal responsive to the operating status being the standard status, the third electrical signal having a third alternating current waveform at a frequency in the range from 50 kHz to 1 MHz.

Illustrative Embodiment 19. The method of Illustrative Embodiment 18, wherein actuating the electric field generator to provide the second electrical signal further comprises actuating the electric field generator to provide the second electrical signal having the second alternating current waveform with a second power greater than a third power of the third electrical signal.

Illustrative Embodiment 20. The method of any of Illustrative Embodiments 18-19, further comprising detecting installation of a generator battery prior to determining an operating status.

Illustrative Embodiment 21. The method of any of Illustrative Embodiments 18-20, further comprising comparing an amount of charge of a first generator battery to an amount of charge of a second generator battery prior to actuating the electric field generator to provide the second electrical signal and prior to actuating the electric field generator to provide the third electrical signal, wherein the second generator battery is a backup battery or a replacement battery for the first generator battery.

Illustrative Embodiment 22. The method of Illustrative Embodiment 21, wherein determining the operating status includes determining the operating status is to include a warning status if the amount of charge of the second generator battery is within 5% of the amount of charge of the first generator battery, and further comprising transmitting a signal indicative of the warning status.

Illustrative Embodiment 23. The method of any of Illustrative Embodiments 18-23, wherein storing the operating parameter further comprises storing data indicative of at least one of a circuit resistance, a voltage of the first alternating current waveform, and a current of the first alternating current waveform prior to deactuating the electric field generator.

Illustrative Embodiment 24. The method of Illustrative Embodiment 23, wherein actuating the electric field generator to provide the second electrical signal is further defined as actuating the electric field generator to provide the second electrical signal based upon the operating parameter wherein either a second initial voltage of the second alternating current waveform or a second current of the second alternating current waveform is selected such that a second power of the second alternating current waveform is between a power of the first alternating current waveform and 95% of the power of the first alternating current waveform.

Illustrative Embodiment 25. An electronic apparatus comprising: an electric field generator providing a first electrical signal having a first alternating current waveform at a frequency between 50 kHz and 1 MHz; and a controller communicating with the electric field generator, the controller having an input, a processor, and a memory storing an accelerated power-up program, a standard power-up program, and computer-executable instructions that cause the processor to: receive a generator power-down event by the input; detect the generator power-down event; deactuate the electric field generator; store an operating parameter indicating whether the electric field generator is operating or not operating; determine an operating status based at least in part on the operating parameter; and actuate the electric field generator to provide a second electrical signal using the accelerated power-up program responsive to the operating status being the accelerated status; the second electrical signal having a second alternating current waveform at a frequency between 50 kHz and 1 MHz.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest themselves to those skilled in the art and which are accomplished within the spirit of the inventive concepts disclosed herein. Modifications and variations are possible in light of the above teachings or may be acquired from practice of the methodologies set forth in the present disclosure.

Even though particular combinations of features and steps are recited in the claims and/or disclosed in the specification, these combinations are not intended to limit the disclosure. In fact, many of these features and steps may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. An electronic apparatus, comprising:

an electric field generator configured to provide a first electrical signal having a first alternating current waveform at a frequency in a range from 50 KHz to 1 MHz; and a controller communicating with the electric field generator to control an output of the electric field generator, the controller having an input, a processor and a non-transitory computer-readable medium storing an accelerated power-up program, a standard power-up program, and computer-executable instructions that when executed by the processor cause the processor to:

receive a generator power-down event by the input, the generator power-down event being a physical interaction with the input;

detect the generator power-down event;

deactuate the electric field generator so as to cease providing the first electrical signal;

store an operating parameter indicative of an operation of the electric field generator or cessation of operation of the electric field generator;

determine an operating status based at least in part on the operating parameter, the operating status being one of an accelerated status and a standard status, the accelerated status indicating that the accelerated power-up program should be executed, and the standard status indicating that the standard power-up program should be executed;

wherein the accelerated power-up program includes computer-executable instructions that when executed by the processor responsive to the operating status being the accelerated status cause the processor to transmit a first control signal to the electric field generator to cause the electric field generator to increase a power of a second alternating current waveform to an operating power over a first time period;

wherein the standard power-up program includes computer-executable instructions that when executed by the processor responsive to the operating status being the standard status cause the processor to transmit a second control signal to the electric field generator to cause the electric field generator to increase a power of a third alternating current waveform to the operating power over a second time period;

wherein, the first time period is less than the second time period; and actuate the electric field generator to provide:

i) a second electrical signal, using the accelerated power-up program responsive to the operating status being the accelerated status, the second electrical signal having the second alternating current waveform at a frequency in the range from 50 kHz to 1 MHz to generate a Tumor Treating Field (TTField); or ii) a third electrical signal, using the standard power-up program responsive to the operating status being the standard status, the third electrical signal having the third alternating current waveform at a frequency in the range from 50 kHz to 1 MHZ to generate the TTField.

2. The electronic apparatus of claim 1, wherein the electric field generator further comprises at least one electrode array port and is further configured to supply power to the at least one electrode array port.

3. The electronic apparatus of claim 1, wherein the generator power-down event includes a generator battery change event that is triggered by one or more of removal of a first generator battery and insertion of a second generator battery.

4. The electronic apparatus of claim 1, wherein the computer-executable instructions further comprise instructions that when executed by the processor cause the processor to store the operating parameter indicative of a deactivation duration of the electric field generator, and wherein determining the operating status includes determining the operating status is the accelerated status when the deactivation duration is below a predetermined deactivation duration threshold.

5. The electronic apparatus of claim 4, wherein the predetermined deactivation duration threshold is 5 minutes.

6. The electronic apparatus of claim 1, wherein the standard power-up program includes computer-executable instructions that when executed by the processor responsive to the operating status being the standard status cause the processor to transmit a control signal to the electric field generator to cause the electric field generator to set an initial power of the third alternating current waveform to less than 95% of an operating power.

7. The electronic apparatus of claim 1, wherein the accelerated power-up program includes computer-executable instructions that when executed by the processor responsive to the operating status being the accelerated status cause the processor to transmit a control signal to the electric field generator to cause the electric field generator to set a power of the second alternating current waveform to between an operating power and 95% of the operating power, inclusive.

8. The electronic apparatus of claim 1, wherein the electric field generator is connected to a first electrode array and a second electrode array, and wherein the computer-executable instructions further comprise instructions that when executed by the processor cause the processor to monitor disconnection of at least one of the first electrode array and the second electrode array wherein, upon detection of a disconnection of at least one of the first electrode array and the second electrode array, the operating status is set to the standard status.

9. The electronic apparatus of claim 1, further comprising:

a first electrode array; and a second electrode array; and wherein the electric field generator is connected to the first electrode array and the second electrode array, and wherein the computer-executable instructions further comprise instructions that when executed by the processor cause the processor to:

store a measurement of circuit resistance as the operating parameter; and monitor a circuit resistance during a period of time in which the electric field generator is deactuated.

10. The electronic apparatus of claim 9, wherein when the monitored circuit resistance differs from the measured circuit resistance stored as the operating parameter by more than a resistance threshold, the operating status is set to the standard status.

11. A method, comprising:

storing an operating parameter, the operating parameter being indicative of an operation of an electric field generator or cessation of operation of the electric field generator, the electric field generator configured to provide a first electrical signal having a first alternating current waveform at a frequency in a range from 50 kHz to 1 MHz;

deactuating the electric field generator so as to cease providing a first electrical signal;

determining an operating status based at least in part on the operating parameter, the operating status being one of an accelerated status and a standard status, the accelerated status indicating that an accelerated power-up program should be executed by a processor, and the standard status indicating that a standard power-up program should be executed by the processor, wherein the accelerated power-up program includes computer-executable instructions that when executed by the processor, responsive to the operating status being the accelerated status, cause the processor to transmit a first control signal to the electric field generator to cause the electric field generator to increase a power of a second alternating current waveform to an operating power over a first time period, wherein the standard power-up program includes computer-executable instructions that when executed by the processor, responsive to the operating status being the standard status, cause the processor to transmit a second control signal to the electric field generator to cause the electric field generator to increase a power of a third alternating current waveform to the operating power over a second time period, wherein, the first time period is less than the second time period; and;

actuating the electric field generator to provide:

i) a second electrical signal, using the accelerated power-up program responsive to the operating status being an accelerated status, the second electrical signal having the second alternating current waveform at a frequency in the range from 50 kHz to 1 MHz to generate a Tumor Treating Field (TTField); or ii) a third electrical signal, using the standard power-up program responsive to the operating status being the standard status, the third electrical signal having the third alternating current waveform at a frequency in the range from 50 kHz to 1 MHz to generate the TTField.

12. The method of claim 11, wherein actuating the electric field generator to provide the second electrical signal further comprises actuating the electric field generator to provide the second electrical signal having the second alternating current waveform with a second power greater than a third power of the third electrical signal.

13. The method of claim 11, further comprising detecting installation of a generator battery prior to determining an operating status.

14. The method of claim 11, further comprising comparing an amount of charge of a first generator battery to an amount of charge of a second generator battery prior to actuating the electric field generator to provide the second electrical signal and prior to actuating the electric field generator to provide the third electrical signal, wherein the second generator battery is a backup battery or a replacement battery for the first generator battery.

15. The method of claim 14, wherein determining the operating status includes setting the operating status to a warning status when the amount of charge of the second generator battery is within 5% of the amount of charge of the first generator battery, and further comprising transmitting a signal indicative of the warning status.

16. The method of claim 11, wherein storing the operating parameter further comprises storing data indicative of at least one of a circuit resistance, a voltage of the first alternating current waveform, and a current of the first alternating current waveform prior to deactuating the electric field generator.

17. The method of claim 16, wherein actuating the electric field generator to provide the second electrical signal is further defined as actuating the electric field generator to provide the second electrical signal based upon the operating parameter wherein either a second initial voltage of the second alternating current waveform or a second current of the second alternating current waveform is selected such that a second power of the second alternating current waveform is between a power of the first alternating current waveform and 95% of the power of the first alternating current waveform.

* * * * *